United States Patent [19]

Dressnandt et al.

[11] Patent Number: 5,741,932
[45] Date of Patent: Apr. 21, 1998

[54] PROCESS FOR PREPARATION OF AJOENE

[75] Inventors: Guenter Dressnandt, München; Heinz Rockinger, Gilching; Helmut Prigge, Wolfratshausen; Arno Treiber, München, all of Germany

[73] Assignee: Consortium für elektrochemische Industrie GmbH, München, Germany

[21] Appl. No.: 555,981

[22] Filed: Nov. 13, 1995

[30] Foreign Application Priority Data

Jan. 13, 1995 [DE] Germany ............ 195 00 863.4

[51] Int. Cl.$^6$ .................. C07C 321/00; C07C 315/00; C07C 7/00; C07C 7/10
[52] U.S. Cl. ................. 568/21; 568/19; 568/22; 585/800; 585/833; 585/836; 585/839
[58] Field of Search ............. 424/195.11; 585/800, 585/833, 836, 839; 568/19, 21, 22

[56] References Cited

U.S. PATENT DOCUMENTS

| | | | |
|---|---|---|---|
| 4,643,994 | 2/1987 | Block et al. | 514/165 |
| 4,665,088 | 5/1987 | Apitz-Castro et al. | 514/420 |

FOREIGN PATENT DOCUMENTS

| | | | |
|---|---|---|---|
| 0185324 | 12/1985 | European Pat. Off. | C07C 147/02 |
| 2948869 | 7/1980 | Germany . | |
| 2061987 | 5/1981 | United Kingdom . | |

OTHER PUBLICATIONS

Chemical Abstracts, vol. 122, No. 10, 1995, Columbus, Ohio, US Abstract No. 109202f2 Gaodeng Xuexiao Huaxue Xuebao., vol. 15, No. 8, 1994, pp. 1172–1174.

Plantatiedica, vol. 56, No. 2, 1990, pp. 202–211, XP000195873, B. Jberl.

Chemical Abstracts, vol. 108, No. 14, Apr. 4, 1988, Columbus, Ohio, US, Abstract No. 118832t & Ihongguo Yaoke Daxue Xuebao, Vol. 18, No. 18, No. 4, 1987, pp. 293–296, W. Yang et al.

Chester, J. Cavallito and John Hays Bailey, J. Am. Chem. Soc. 66, (1944), 1950–1951; Allicin, the Antibacterial Principle of Allium sativum. I. Isolation, Physical Properties and Antibacterial Action.

Small, L.V.D., Bailey, J.H. Cavallito C.J., J. Am. Chem. Soc. 69, (1947), 1710–1713.

*Primary Examiner*—Marian C. Knode
*Assistant Examiner*—Ali R. Salimi
*Attorney, Agent, or Firm*—Collard & Roe, P.C.

[57] ABSTRACT

A process for the preparation of ajoene using cyclodextrin comprising mixing allicin, where appropriate dissolved in water and/or a water-miscible solvent, with α-cyclodextrin, β-cyclodextrin, γ-cyclodextrin or any desired mixture of these cyclodextrins; and processing to a water-containing composition; drying this composition; and obtaining the resulting ajoene by decomplexation and extraction from the dried composition.

6 Claims, 1 Drawing Sheet

Microbiological results with Ajoen, Allicine and Diallyldisulfide by "bacillus subtilis"-cultures Microbiological test with bacillus subtilis of:
1 = Allicine       concentration: 800 µg/ml
2 = Diallyldisulfide concentration: 800 µg/ml
3 = Ajoen         concentration: 800 µg/ml

PROCESS FOR PREPARATION OF AJOENE

BACKGROUND OF THE INVENTION

1. Field of the Invention

The present invention relates to a process for the preparation of ajoene using cyclodextrin.

2. The Prior Art

Garlic has been for millennia an important seasoning and foodstuff but also one of the best known and most widely used remedies in the folk medicine of many peoples. However, even today, it is still frequently taken, increasingly in recent times, as an effective remedy for a large number of disorders such as, for example, for various infectious diseases, for some metabolic disorders and, in particular, for cardiovascular disorders. Its curative effects have also been confirmed by the pharmacological research which has been carried on vigorously in recent decades.

It is known from the chemistry and pharmacology of garlic that the principal constituent of the parent substance alliin [(+)-S-allyl-L-cysteine sulfoxide] itself has no pharmacological activity. It is furthermore known that, of the secondary products produced by enzymatic degradation on comminution of garlic, only allicin (allyl-2-propenethiosulfinate) and, of the secondary products produced by conversion of allicin into organic sulfur compounds, only ajoene (4,5,9-trithiadodeca-1,6,11-triene-9-oxide) and, in part, also the vinyl-dithiin which is produced in small amounts, have high pharmacological activity.

None of the other secondary products show therapeutic activity.

Thus, according to the current state of knowledge, allicin and ajoene and, in part, also dithiin are by far the therapeutically most important active substances in garlic.

Despite their demonstrated therapeutic activity, these substances have not to date been used as standardized therapeutic agents for the following reasons:

Allicin can easily be obtained by isolation from garlic or by synthesis but is very unstable and is easily and rapidly converted into secondary products, which are usually inactive, such as diallyl disulfide and polysulfides.

DE-C 2,948,869 (corresponds to GB 2,061,987) therefore attempted to complex allicin, with exclusion of oxygen, with cyclodextrins in order thereby to obtain inclusion complexes of cyclodextrin and allicin which are more stable than allicin itself. Furthermore, DE-C 2,948,869 describes the use of the cyclodextrin/allicin complexes as pharmaceutical products. As is evident from the examples in the application, although the stability of the complexes is greater than the stability of allicin, it is still too low for them to be suitable as pharmaceutical products with long-term stability. In addition, pure active substances, not those in complex form, are desirable for pharmaceutical use.

To date it has not been possible to prepare an allicin product which has long-term stability and is thus standardizable.

Although ajoene is very stable and therefore suitable for standardizable products, obtaining it is a problem because it can be obtained from allicin only in small yields under time-consuming or costly conditions.

The preparation of ajoene is disclosed for example, in U.S. Pat. No. 4,665,088, EP-A 185,324, or U.S. Pat. No. 4,643,994. All the known processes are based in principle on partial conversion of allicin to ajoene in organic solvents and subsequent extraction and isolation of this active substance from the large number of secondary products obtained. It is disadvantageous that all these conversion processes have only low selectivity for ajoene, and the yield of ajoene is very low.

To date, no economical process for obtaining ajoene has been disclosed.

SUMMARY OF THE INVENTION

It is an object of the present invention to provide an economic process for obtaining ajoene which avoids the disadvantages of the prior art.

The object is achieved by a process according to the invention which comprises mixing allicin, where appropriate dissolved in water and/or a water-miscible solvent with α-cyclodextrin, β-cyclodextrin, γ-cyclodextrin or any desired mixture of these cyclodextrins; and processing to a water-containing composition; drying this composition; and obtaining the resulting ajoene by decomplexation and extraction from the dried composition.

In a preferred embodiment, the dried product is treated before the decomplexation with an anhydrous organic solvent. This step considerably increases the yield of ajoene.

The process according to the invention makes it possible to provide the pharmacologically highly active substance ajoene in amounts which make it possible to prepare an ajoene containing standardizable remedy.

The advantages of the process according to the invention by comparison with known methods for preparing ajoene are the considerably higher yield, the good reproducibility and the ease of industrial implementation of the process.

Because of the known instability of allicin, the process according to the invention is preferably carried out using a fresh aqueous solution of allicin.

Since allicin is not commercially available because of its instability, it is preferably either isolated from garlic or prepared by known processes, for example by oxidation of diallyl disulfide, which can be purchased (Cavallito, C. J., Bailey, J. H., *J. Am. Chem. Soc.* 66, (1944), 1950–1951; Small, L. V. D., Bailey, J. H., Cavallito C. J., *J. Am. Chem. Soc.* 69, (1947), 1710–1713).

To improve the stability of allicin, it is advantageous to use the allicin diluted in a suitable solvent in the process according to the invention.

Suitable solvents for allicin are water and/or all water-miscible solvents whose use does not additionally endanger the low stability of allicin. Examples of such solvents are lower ($C_1$ to $C_4$) alkanols or ketones. Water, ethanol or an ethanol/water mixture in the ratio 1:1 to 1:99 is preferably used as a solvent. Since the concentration of the allicin in the solvent also greatly affects the stability of allicin, preferably highly diluted allicin solutions are used.

Allicin is therefore particularly advantageously used in the process according to the invention as an approximately 1% strength aqueous or aqueous/alcoholic solution.

In this form, allicin can be stored for a lengthy period at low temperatures of, preferably, −30° C. or below.

α-, β- or γ-Cyclodextrin, singly or in any desired mixture, can be used in the process according to the invention.

β-Cyclodextrin and/or γ-cyclodextrin are particularly suitably used.

The cyclodextrins can be used as an aqueous solution, as concentrated suspension or paste or in powder form. As aqueous solution, they are preferably used as a saturated solution.

Cyclodextrin and allicin are preferably mixed in a molar ratio of from 1:2 to 1:0.5, particularly preferably from 1:1.2 to 1:0.8.

The mixing of the cyclodextrin or of the cyclodextrin solution or suspension or paste with the allicin solution is carried out at 2°–70° C., preferably with initial temperatures of 30°–50° C. and with a slow cooling to 2° to about 20° C. in a conventional way, for example, by stirring.

The mixing takes place preferably over a period of from 1 to 48 hours, particularly preferably from 2 to 4 hours.

The mixing process can be carried out under normal conditions (air) or with exclusion of oxygen in the presence of an inert gas, for example nitrogen. It is usually carried out under normal conditions, that is to say in the presence of air.

The resulting homogenous mixture is dried as such by any suitable method customary in practice. For example, the mixture is dried at room temperature in the air or under vacuum at 20° to 120° C., preferably at 30° to 90° C., or by freeze drying or by spray drying.

To increase the yield of ajoene, it is advantageous to treat the resulting dry product with an anhydrous organic solvent.

Solvents suitable in this respect are, preferably, anhydrous ethers, lower alkanols, ketones or chlorohydrocarbons. Anhydrous diethyl ether is particularly suitable.

The dry product is preferably mixed with the solvent all at once or in 2 to 3 partial quantities in the total ratio 1:60 to 1:3 for a total period of 60 to 300, preferably 90 to 180, minutes at room temperature (about 20° C.) or by boiling under reflux conditions, and subsequently dried after stripping off the solvent (for example in a rotary evaporator under vacuum) in a manner known per se. The drying can take place, for example, in a vacuum drying oven at 30° to 120° C.

The ajoene is formed in the complex in 2 isomeric forms (cis, trans) and is extracted from the dry product by customary decomplexation methods and is isolated, for example, with the aid of a suitable solvent.

It can subsequently be further purified by means of separation processes known per se, for example a suitable chromatographic separation process.

All decomplexation methods are based on dissolving or suspending the complexes in a large amount of water and extracting the entrapped guest substance from the aqueous phase using a non-polar solvent, and recovering from the extract.

Ajoene is thus obtained according to the invention from the ajoene/cyclodextrin complex by decomplexation with mixtures of water and at least one non-polar organic solvent, separation of the organic phase and the aqueous phase, obtaining the ajoene from the organic phase, for example, by drying.

Suitable organic solvents are all known solvents for ajoene such as, for example, ethers or chlorohydrocarbons. Diethyl ether and petroleum ether are suitable and preferred.

After removal of the aqueous phase, the organic phase obtained in this way is dried by known processes.

The ajoene can subsequently, if required, be further purified by known processes such as, for example, by preparative HPLC.

The degree of conversion of allicin into ajoene in the presence of cyclodextrins depends both on the cyclodextrin used and on the conditions of complexation and after-treatment. It is greatest under the said preferred conditions and, in particular, when the cyclodextrin complex is treated with an anhydrous organic solvent, preferably an ether.

The ajoene formed in the process according to the invention by conversion of allicin can be used both in the complex form as cyclodextrin/ajoene complex and in pure form.

The invention therefore also relates to complexes of $\alpha$-, $\beta$-, or $\gamma$-cyclodextrin with ajoene.

The drug sector is the principal area of use to be considered for the cyclodextrin/ajoene complexes or the ajoene prepared according to the invention. It can be used therein as stable and therefore standardizable product, particularly for cardiovascular disorders such as, for example, arteriosclerosis, thrombotic events, high blood pressure inter alia, and for various bacterial infections and as remedy for some organic and metabolic disturbances.

As preventive health remedy it can, of course, also be used in the foodstuffs sector.

BRIEF DESCRIPTION OF THE DRAWINGS

Other objects and features of the present invention will become apparent from the following detailed description considered in connection with the accompanying drawing and Examples which discloses several embodiments of the present invention. It should be understood, however, that the drawing is designed for the purpose of illustration only and not as a definition of the limits of the invention.

In the drawing, wherein similar reference characters denote similar elements throughout the several views.

Figure 1:
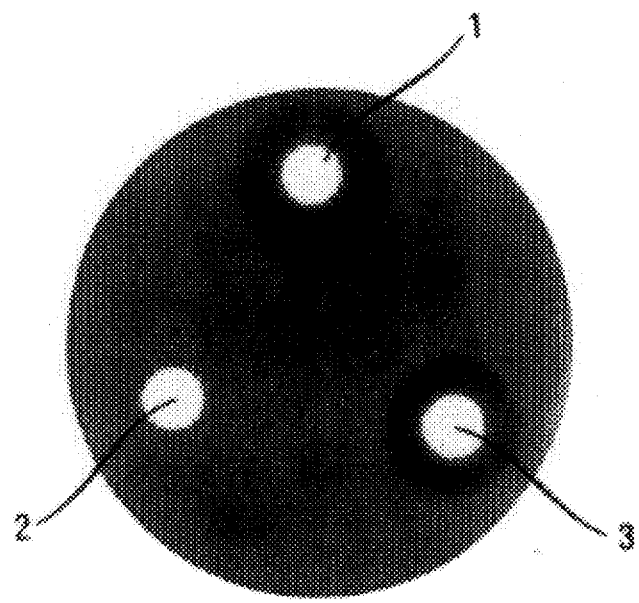
FIG. 1 shows the pictures of zones of inhibition described in Example 8. The meanings are.

| 1 = Allicin | Concentration: 800 µg/ml |
| 2 = Diallyl disulfide | Concentration: 800 µg/ml |
| 3 = Ajoene | Concentration: 800 µg/ml |

The allicin used in the examples was isolated from fresh garlic by the method described by Cavallito (Cavallito, C. J., Bailey, J. H., *J. Am. Chem. Soc.* 66, (1944), 1950–1951).

Analytical tests in the examples were carried out by HPLC and by $^1$H-NMR and $^{13}$C-NMR.

EXAMPLE 1

10 g of $\alpha$-cyclodextrin (water content 8.4%) were introduced as powder into a mortar and homogeneously mixed in portions with a total of 70 ml of an aqueous solution which contains 0.526 g of crude, 97.3% pure allicin. The resulting white paste was homogenized by further stirring for two hours, subsequently dried in the air at room temperature, and then ground to a fine powder. 10.5 g of product were obtained.

This intermediate product was dissolved in 3000 ml of water with vigorous stirring over the course of 5 hours. The slightly cloudy solution was then extracted three times with 500 ml of diethyl ether each time. Water was then removed from the combined ether extract freezing out ($CO_2$/acetone bath), and the extract was then concentrated in a rotary evaporator under vacuum to remove the ether.

The 0.45 g of residue obtained in this way contains, according to $^1$H-NMR analysis, 30.5% of ajoene based on the allicin used (about 0.156 g) (10.3% cis-ajoene, 20.2% trans-ajoene).

EXAMPLE 2

10 g of $\beta$-cyclodextrin (water content 10%) were homogenized with 0.87 g of 79.2% pure allicin and subsequently triturated with 13 ml of water to give a homogeneous paste. The latter was dried under vacuum at 20° C.

9.67 g of dry product (residual water content=3%) were obtained and were powdered by grinding, washed with ether and dried.

The ajoene was obtained from the complex by dissolving the product obtained in this way in 3000 ml of water (vigorous stirring for 5 hours) and subsequently extracting etc. as described in Example 1.

The residue from the collected ether extracts amounted to 0.42 g. The ajoene yield was 49.5% based on allicin used (about 0.34 g). It consisted of 37.1% cis- and 12.4% trans-ajoene.

EXAMPLE 3

The process was carried out as in Example 2 but with the difference that crude, 78.8% pure allicin used was employed diluted with 96% strength ethanol (ratio 1:1), the drying took place under vacuum at 30° C., the finely powdered dry product was boiled under reflux with 100 ml of diethyl ether for 4 h before the decomplexation, and the decomplexation was carried out by dissolving in 300 ml of water and extracting 3 times with 100 ml of ether each time, likewise by boiling under reflux. The extraction residue of 0.9 g contained 69.8% ajoene based on the allicin used. It consisted of 34.0% cis-ajoene and 35.8% trans-ajoene.

A 98% pure ajoene concentrate with the same cis/trans ratio was obtained by dissolving in water and extracting with n-heptane and diethyl ether and by preparative HPLC.

EXAMPLE 4

The procedure described in Example 3 was followed, with the only exception that α-cyclodextrin was used.

The extraction residue of 0.8 g contained 37.4% ajoene, consisting of 14.2% cis-ajoene and 23.2% trans-ajoene, based on the amount of allicin used.

EXAMPLE 5

10 g of β-cyclodextrin (water content=10%) were dissolved in 200 ml of water at 50° C. while flushing with $N_2$. While continuing to flush with $N_2$, 1.41 g of allicin were added dropwise as 16% strength ethanolic solution to this cyclodextrin solution, and the mixture was stirred at 50° C. for 30 minutes. This mixture was cooled, while continuing to stir, at 2° C. over the course of 20 hours, and was freeze-dried in its entirety.

9.5 g of fine-particle powder were obtained, and from this were subsequently obtained, by decomplexation, 1.06 g of crude product with an ajoene content of 29.2%, consisting of 23.1% cis-ajoene and 6.1% trans-ajoene, based on the allicin used.

The decomplexation was carried out as follows: the freeze-dried powder (9.5 g) was boiled under reflux with 600 ml of water, which had been slightly acidified (pH 2–3) with HCl, for 1.5 h. The resulting solution was extracted by shaking three times with 200 ml of ether each time. Water was removed from the combined ether extract by freezing out, and the extract was concentrated under vacuum.

EXAMPLE 6

The procedure described in Example 5 was followed up to the freeze-drying.

The freeze-dried powder was shaken three times with 150 ml of diethyl ether each time for 30 min and subsequently dried in a vacuum drying oven.

The 9.5 g of fine-particle powder obtained in this way were extracted as described in Example 5. 1.06 g of crude product with an ajoene content of 85% based on allicin used were obtained.

EXAMPLE 7

10 g of γ-cyclodextrin were dissolved in 43 ml of water at 40° C. with stirring. After this cyclodextrin solution had been cooled to 10° C., 100 ml of a 1% strength aqueous allicin solution were added dropwise. After stirring for a further 19 hours, the precipitate which had separated out was filtered off and dried. 7.2 g of dry powder were obtained. This was shaken three times with 150 ml of diethyl ether each time for 30 min and then dried in a drying oven.

Subsequently the ajoene was extracted from this dry powder by decomplexation as described in Example 1. Determination of ajoene in the resulting 0.9 g of extraction residue showed 0.457 g. This corresponds to an ajoene yield of 45.7%.

EXAMPLE 8

The inhibitory effect of ajoene prepared as in Example 3, and of allicin and diallyl disulfide on the growth of test bacteria (*Bacillus subtilis*) was tested on a nutrient medium (LB medium) infected therewith.

For this purpose, firstly 20 ml of a nutrient medium solution (LB medium) were poured into a sterile Petri dish with a diameter of 10 cm. After solidification of the layer which was about 1 cm thick, a layer about 1 mm thick of bacterial culture (*Bacillus subtilis*) was placed on top (solution a+b), and the filter disk (about 10 mm diameter) impregnated with 40 μl of the substance solution to be investigated was placed on top of this using sterile forceps. The solution was left to act on the bacterial layer in a refrigerator (5° C.) for about 2 hours and then incubated at 28° C. for about 16 hours. The zone of inhibition formed around the filter disk was measured (diameter or width) and photographed. It represents a criterion for the antibacterial activity of the tested substance.

Solution a=Nutrient solution (LB liquid)

10 g of tryptone 5 g of yeast extract 5 g of NaCl were made up with water to 1 l and sterilized Solution b=LB soft agar 5 g of tryptone 2.5 g of yeast extract 2.5 g of NaCl 3.0 g of agar were made up with water to 1 l and sterilized The filter paper disks were likewise sterilized at 120° C. for 20 min.

Preparation of the *Bacillus subtilis* culture 1 ml of *Bacillus subtilis* initial culture solution is pipetted into an Erlenmeyer flask containing 10 ml of nutrient solution (solution a), and the culture is grown in a shaking waterbath at 260 rpm at 37° C. overnight.

0.1 ml of this *Bacillus subtilis* solution is added to 10 ml of soft agar (solution b) which has been liquified by gentle warming, and is mixed by brief swirling and is layered onto the nutrient medium in the dish.

This amount is sufficient for 1 Petri dish.

The pictures of the zones of inhibition depicted in FIG. 1 show that at active substance concentrations of 800 μg/ml, the antibacterial inhibitory effects obtained with ajoene are as good as those with allicin, while no effect at all is obtained on use of diallyl disulfide, the main component of "garlic oil".

While several embodiments of the present invention have been shown and described, it is to be understood that many changes and modifications may be made thereunto without departing from the spirit and scope of the invention as defined in the appended claims.

What is claimed is:

1. A process for obtaining ajoene, which comprises the steps of mixing allicin or allicin dissolved in a solvent selected from the group consisting of water, a water-miscible solvent, and the mixtures thereof; with a cyclodextrin selected from the group consisting of α-cyclodextrin, β-cyclodextrin, γ-cyclodextrin and the mixtures thereof;

processing to a water-containing composition;

drying said composition; and obtaining the resulting ajoene by decomplexation and extraction from the dried composition.

2. The process as claimed in claim 1, comprising treating the dried composition before the decomplexation with an anhydrous organic solvent.

3. The process as claimed in claim 2, wherein said anhydrous organic solvent is an ether.

4. The process as claimed in claim 3, wherein diethyl ether is employed as said ether.

5. The process as claimed in claim 1, wherein allicin is utilized as an approximately 1 % strength aqueous solution.

6. The process as claimed in claim 1, wherein said cyclodextrin is selected from the group consisting of β-cyclodextrin, γ-cyclodextrin, and the mixtures thereof.

* * * * *